US00PP25494P2

(12) United States Plant Patent
Richards

(10) Patent No.: US PP25,494 P2
(45) Date of Patent: Apr. 28, 2015

(54) ***HELIANTHUS* PLANT NAMED 'DOUBLE WHAMMY'**

(50) Latin Name: *Helianthus decapetalus×multiflorus*
Varietal Denomination: Double Whammy

(71) Applicant: Rodney Richards, Hereford (GB)

(72) Inventor: Rodney Richards, Hereford (GB)

( * ) Notice: Subject to any disclaimer, the term of this patent is extended or adjusted under 35 U.S.C. 154(b) by 85 days.

(21) Appl. No.: 13/987,736

(22) Filed: Aug. 27, 2013

(51) Int. Cl.
*A01H 5/00* (2006.01)

(52) U.S. Cl.
USPC ..... Plt./436

(58) Field of Classification Search
CPC ..... A01H 5/025; A01H 5/02; A01H 5/00
USPC ..... Plt./436
See application file for complete search history.

*Primary Examiner* — Kent L Bell
(74) *Attorney, Agent, or Firm* — Penny J. Aguirre

(57) ABSTRACT

A new cultivar of *Helianthus*, 'Double Whammy', that is characterized by its upright and compact plant habit, its large inflorescences that are golden yellow in color, and its double inflorescences with a row of ray florets on the outer edge and disc florets with expanded petals (ray floret-like) that are uniformly formed throughout bloom.

2 Drawing Sheets

Botanical classification: *Helianthus decapetalus×multiflorus*.

Variety denomination: 'Double Whammy'.

BACKGROUND OF THE INVENTION

The present invention relates to a new and distinct cultivar of *Helianthus decapetalus×multiflorus* and will be referred to hereafter by its cultivar name, 'Double Whammy'. 'Double Whammy' represents a new *Helianthus*, an herbaceous perennial grown for landscape use.

The Inventor discovered the new *Helianthus* as a naturally occurring whole plant mutation in 2009 in a nursery bed in Pukekohe, New Zealand. The parentage is unknown, however based on its characteristics, the new cultivar is an interspecific hybrid between *Helianthus decapetalus* and *Helianthus multiflorus*.

Asexual propagation of the new cultivar was first accomplished by division by the Inventor in Mansell Gamage, Hereford, United Kingdom in spring of 2011. Asexual propagation by division and stem cuttings has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Double Whammy' as a unique cultivar of *Helianthus*.

1. 'Double Whammy' exhibits an upright and compact plant habit.
2. 'Double Whammy' exhibits large inflorescences that are golden yellow in color.
3. 'Double Whammy' exhibits double inflorescences with a row of ray florets on the outer edge and disc florets with expanded petals (ray florets like) that are uniformly formed throughout bloom.

Typical plants of *Helianthus decapetalus*, a probable parent plant, differ from 'Double Whammy' in having single flowers with typical disc florets, in having leaves that are elliptic in shape with a more pronounced acuminate apex and greater pubescence, and in having a more spreading plant habit. Typical plants of *Helianthus multiflorus*, a probable parent plant, differ from 'Double Whammy' in having double inflorescences that lack a distinct row of outer rays florets (*Dahlia* like) and in having longer stems and wider leaves. 'Double Whammy' can be most closely compared to the cultivars 'Sunshine Daydream' (not patented) and 'Loddon Gold' (not patented). 'Sunshine Daydream' is similar to 'Double Whammy' in having double inflorescences that are similar in color. 'Sunshine Daydream' differs from 'Double Whammy' in having inflorescences that lack a distinct row of ray florets and are more dome-shaped. 'Loddon Gold' is similar to 'Double Whammy' in having double inflorescences. 'Loddon Gold' differs from 'Double Whammy' in having inflorescences that are more yellow in color with less distinct ray florets, in blooming later in the season, and in having a taller plant height.

BRIEF DESCRIPTION OF THE DRAWINGS

The accompanying colored photographs illustrate the overall appearance and distinct characteristics of the new *Helianthus*. The plants in the accompanying photographs were taken of a plant about two years in age as grown in a garden in Mansell Gamage, Hereford, United Kingdom.

The photograph in FIG. 1 depicts a plant of 'Double Whammy' in bloom.

Figure 1:
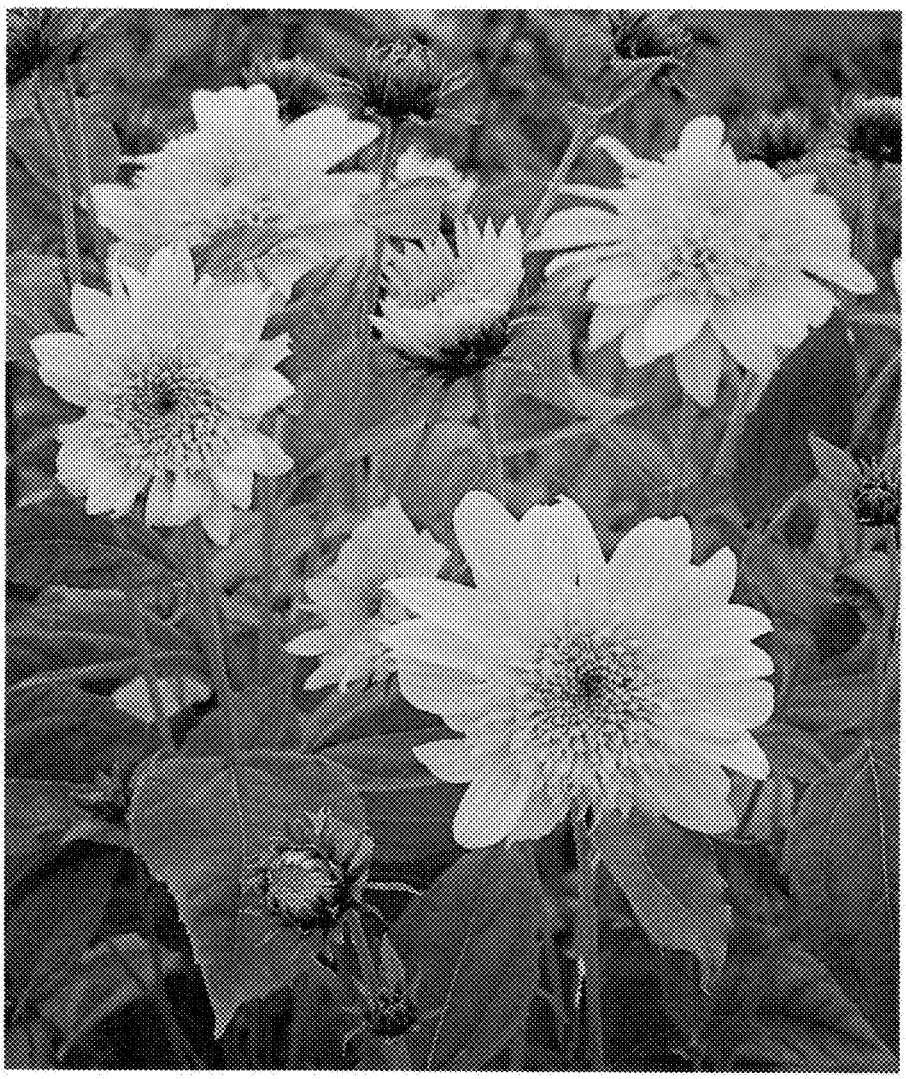
Figure 2:
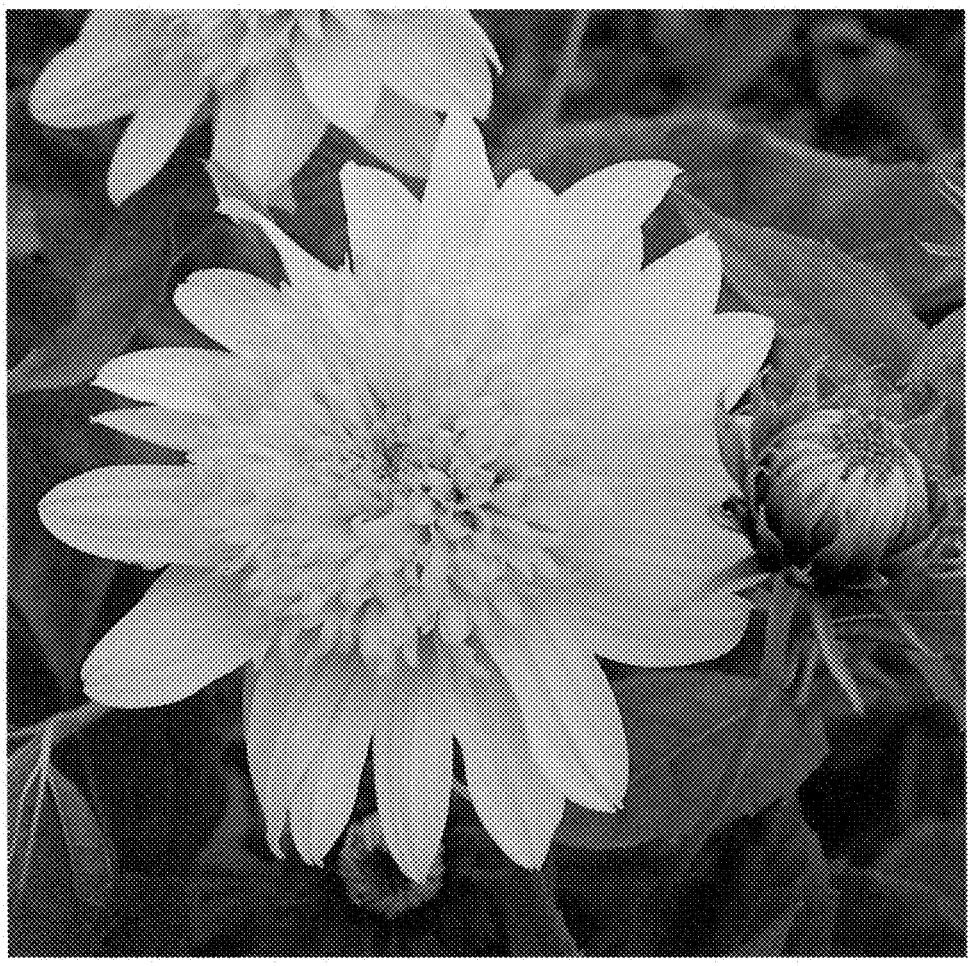

The photograph in FIG. 2 shows a close-up of the inflorescences of 'Double Whammy'.

The inflorescences are golden yellow in color and the reddish tinge in the photographs is due to shading of the dense florets. The colors in the photographs may differ slightly from the color values cited in the detailed botanical description, which accurately describe the colors of the new *Helianthus*.

BOTANICAL DESCRIPTION OF THE PLANT

The following is a detailed description of the new cultivar with the data taken from plants 10 months in age (from a rooted liner) as grown in two-gallon containers in Watsonville, Calif. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—4 to 6 weeks in late July to late August and can extend into September in the United Kingdom.

*Plant type.*—Herbaceous perennial.

*Plant habit.*—Upright and compact.

*Height and spread.*—Reaches about 1.2 m in height and about 76 cm in spread in the landscape.

*Hardiness.*—At least in U.S.D.A. Zone 5B.

*Diseases and pests.*—No susceptibility or resistance to diseases or pests has been observed.

*Root description.*—Fibrous.

*Propagation.*—Stem cuttings preferred.

*Growth rate.*—Moderate to vigorous.

Stem description:

*Shape.*—Slightly oval.

*Stem color.*—Main stem; a blend of 144A and 144B; lateral stems; 144B.

*Stem size.*—Main stem; an average of 38 cm in length and 7 mm in diameter, lateral branches; an average of 15 cm in length and 2 mm in width.

*Stem surface.*—Main stem; slightly pubescent with fine ridges, lateral stems; slightly pubescent.

*Stem number and branching.*—An average of 7 main stems with an average of 7 lateral stems per main stem.

*Internode length.*—An average of 2 cm.

Foliage description:

*Leaf shape.*—Ovate.

*Leaf division.*—Simple.

*Leaf base.*—Truncate and slightly rounded.

*Leaf apex.*—Acuminate.

*Leaf venation.*—Pinnate, 145A on upper surface and lower surface.

*Leaf margins.*—Serrate.

*Leaf attachment.*—Petiolate.

*Leaf arrangement.*—Alternate.

*Leaf size.*—Matures to an average of 10 cm in length and 7.5 cm in width.

*Leaf color.*—Young leaves; upper surface 137A, lower surface 138A, mature leaves; upper surface N189A, lower surface 147A.

*Leaf surface.*—Both surfaces dull and sparsely pubescent.

*Stipules.*—None.

Flower description:

*Type.*—Capitulum, double with a row of ray florets around the margin and showy disc florets in the center (expanded petals), relatively flat in aspect.

*Capitulum number.*—An average of 12 capitulums per stem emerging from nodes from the apex to the base with new blooms opening throughout the bloom period.

*Lastingness of inflorescence.*—About 10 days.

*Capitulum size.*—About 8 cm in depth and 2.5 cm in diameter, disc size is about 2 cm in depth and 4.8 cm in diameter.

*Fragrance.*—None detected.

*Involucral bracts or phyllary.*—About 36 arranged in 3 overlapping rows, up to 1.2 cm in length and 3 mm in width, fused at base, acuminate apex, lanceolate in shape, 137A in color, entire ciliate margin and slightly puberulent on both surfaces, held slightly reflexed.

*Buds.*—Globose in shape, average of 2 cm in diameter and height, color; phyllary are 137A, ray florets are 7A, disc floret portion 145A.

*Peduncle.*—Strong, held upright to a 30° angle from stem (0° vertical), an average of 15 cm in length and an average of 2 mm in diameter, 144C in color, pubescent surface.

*Ray florets* (*sterile*).—Average of 20, elliptical in shape, vertical ridges on both surfaces, about 1.6 cm in length and 1.2 cm in width, acute apex, broadly cuneate base, entire margin, glabrous on upper and lower surface, initially held slightly upright and become horizontal, then slightly downward as they mature, color of upper and lower surface when opening and fully open; 9A, color of upper and lower surface when drying; 15A.

*Disc florets* (*bisexual and sterile*).—Numerous, about 400, tubular in shape, arranged spirally on a disk receptacle to form a cushion shaped mound, florets are about 2.5 mm in length and 5 mm in width, petals (5) are fused into tube about 1.5 cm in length and 5 mm in width and 7A in color on both surfaces, most have single expanded petals and are sterile (ray floret-like) and are an average of 2.8 cm in length and 7 mm in width with same characteristics as ray florets, campanulate calyx (fused sepals), about 1.5 mm in width and length, glabrous on outer and inner surface, and 1C in color.

Reproductive organs (fertile disc florets only):

*Gynoecium.*—Pistil; 1, 1 cm in length, style; 9 mm in length, 1C in color, surrounded by stamens at base, stigma; bifid, each arm is curled, about 1 mm in length and 7A in color, ovary; inferior, oblong in shape, 4 mm in length and 1.5 mm in width, glabrous surface, NN155C in color.

*Androcoecium.*—Stamens; 5, fused, form a cylinder around base of style, about 5 mm in length and 0.3 mm in width, filaments are minute and 7B in color, stamens are 200D in color, pollen is low in quantity and 11A in color.

*Seed.*—Fertile seed development has not been observed.

It is claimed:

1. A new and distinct cultivar of *Helianthus* plant named 'Double Whammy' substantially as herein illustrated and described.

* * * * *